United States Patent [19]
Wang

[11] Patent Number: 5,730,138
[45] Date of Patent: Mar. 24, 1998

[54] METHOD AND APPARATUS FOR DIAGNOSING AND MONITORING THE CIRCULATION OF BLOOD

[76] Inventor: Wei-Kung Wang, No. 14, Sublane 3, Lane 61 Yen Chiu Yuan Road, Sec. 2, Nan Kang District, Taipei, Taiwan

[21] Appl. No.: 520,820

[22] Filed: Aug. 30, 1995

Related U.S. Application Data

[63] Continuation-in-part of Ser. No. 82,922, Jun. 25, 1993, abandoned, which is a continuation-in-part of Ser. No. 770,786, Oct. 4, 1991, abandoned, which is a continuation of Ser. No. 301,811, Jan. 25, 1989, abandoned, which is a continuation-in-part of Ser. No. 166,419, Mar. 10, 1988, abandoned.

[51] Int. Cl.$^6$ .................................................. A61B 5/00
[52] U.S. Cl. ................... 128/672; 128/687; 128/690
[58] Field of Search ................................. 128/672, 687, 128/690, 691, 748, 668

[56] References Cited

U.S. PATENT DOCUMENTS 5,365,930  11/1994  Takashima et al. ................... 128/687
5,381,797  1/1995  Pak et al. ............................. 128/687

*Primary Examiner*—Robert L. Nasser
*Attorney, Agent, or Firm*—Ladas & Parry

[57] ABSTRACT

A method and apparatus for diagnosing the circulation of blood. A pressure measurement instrument is provided to measure the waveform of the blood pressure in an artery of a patient. An analyzer is employed to analyze the frequency components of the blood pressure wave in order to compare the pattern of each resonance component to the pattern of a normal blood pressure wave in order to determine whether the blood distribution of the patient is off-balance. This off-balance can be diagnosed from the Chinese medicine principles by relating each harmonic in the blood pressure wave to the corresponding meridian which includes a specific organ. If a specific problem or disorder is identified, the effectiveness of any treatment can be monitored by following the change in the specific harmonic component in the blood pressure wave. This method can also be a valuable medical tool in the development of new treatments or drugs. The analyzer includes a device for analyzing the amplitude and the phase of the resonant frequencies in the blood circulation of the body, and includes a transducer attached to or closely adjacent to the surface of an artery of the body of the patient. The analyzer includes a computer for analyzing the frequency spectrum of blood pressure in the artery for determining characteristics of the frequencies of the meridians of the body and for diagnosing whether the meridian is in trouble.

15 Claims, 1 Drawing Sheet

METHOD AND APPARATUS FOR DIAGNOSING AND MONITORING THE CIRCULATION OF BLOOD

This application is a continuation-in-part of Ser. No. 08/082,922, filed Jun. 25, 1993, now abandoned, which is a continuation-in-part of Ser. No. 07/770,786, filed Oct. 4, 1991, now abandoned, which is a continuation of Ser. No. 07/301,811, filed Jan. 25, 1989, now abandoned, which is a continuation-in-part of Ser. No. 07/166,419, filed Mar. 10, 1988, now abandoned.

BACKGROUND OF THE INVENTION

1. Field of the Invention

This invention relates to a method and apparatus for determining and analyzing the blood pressure wave spectrum associated with the blood flow in a human being, and relating each characteristic resonant frequency of the spectrum to a corresponding meridian or organ of the human body.

2. Brief Description of the Prior Art

The circulatory system of the human body is a pressure inflated system; pressure waves are propagating over the entire artery distribution system to drive the blood into tissue. Since Harvey in 1682 (Harvey, W., *Exercitatio Anatomica de Motu Cordis et Sanguinis in Animalibus,* an English translation with annotations by C. D. Leake, 4th ed. Charles C. Thomas, Springfield, 1958) found that the blood is circulated in a closed system, there have been many important discoveries in the West, such as: Windkessel's model (Hales, S., *Statistical Essays containing Haemostatisicks,* Innays and Manoy, London, 1733, reprinted by Hafner Publishing Co., New York, 1964); the derivation of wave propagation in elastic arteries (Young, T., *The Croonian Lecture on the Function of the Heart and the Arteries,* Phil Trans., London, 1809, reprinted in *Works of Thomas Young,* ed. Peacock, G., vol. 1, John Murray Ltd., London, 1855); the frequency dependence of arterial trees (Engelberg, J., and Dubois, A. B., *Mechanics of Pulmonary Circulation in Isolated Rabbit Lungs,* Am J. of Physiology, vol. 196, pp. 401, 1959); and (Shaw, D. B., *Compliance and Inertance of the Pulmonary Arterial System.* Clin. Sci., vol. 25, pp. 181, 1963), to name a few.

The development of theories in hemodynamics mainly rely on the Navier-Stokes equation which is the flow equation describing the movement of a portion of the fluid under all kinds of forces. Womersley J. R. is the most cited scientist in this field. The impedance works developed in later years depended mostly on his works. Since the equations are essentially flow equations, the heart was also considered as a flow pump (see *Hemodynamics,* W. R. Milnor, William Wilkins, 1989, or *Biodynamics,* Y. C. Fung, Springer Verlag, 1984). It becomes obscure to discover that more than 95% of the energy in the circulatory system is stored in the form of elastic energy, and the kinetic energy of blood flow constitutes less than 5% of the total energy. Another interesting phenomenon is that the systolic pressure in the aorta, large artery, or even small artery are not decreased downstream of the heart pump; they are mildly increased instead (*Blood Flow in Large Artery,* McDonald D. A., Arnold, 1960). All these examples suggested that simple flow theories, which were derived for river or tap water flow where the potential energy is constantly decreasing as the water travels downstream, cannot fully describe the blood circulatory system of the human body.

In the Orient, the written record of blood circulation theory was started no later than one thousand years B.C. during the Chou dynasty, when the method of pulse feeling was developed. The theory of pulse feeling was based on the idea that by feeling the pulse at different points on the body, one may feel the condition of the nine internal organs.

SUMMARY OF THE INVENTION

Despite the success of pulse feeling, it was not until Wang et al. (Wang W. K., Wang Lin Y. Y., Hsu T. L., and Ching Y., *Some Foundation of Pulse Feeling in Chinese Medicine,* Biophysics Laboratory, Institute of Physics, Academia Sinica, Taipei, Taiwan, 11529, R.O.C.; Wang W. K., Lo Y. Y., Chiang Y., Hsu T. L., and Wang Lin Y. Y., *Resonance of Organs with the Heart.* Biophysics Laboratory, Institute of Physics, Academia Sinica, Taipei, Taiwan, 11529, R.O.C.) discovered the relationship between harmonics in the blood pressure wave in the artery and the circulation of the blood to the various body organs, that the workings of Chinese pulse feeling could be explained.

According to the discovery, the pulse feeling of Chinese medicine was found to be from the harmonic resonance of the heart and arteries with the body's organs or tissues. The blood will flow into an organ if the impedance of the organ is minimized, which impedance would be minimum at a specific frequency. Therefore, if the blood flow is reduced due to some impedance mismatch, it will indicate that the organ is not healthy, and this can be determined by analyzing the sensing characteristics of the blood pressure wave which, in fact, are reflective of the relative change in amplitude, frequency, or phase, of the harmonic components of the blood pressure wave spectrum, rather than simply "feeling" the pulse. With proper training and experience, one thus can determine which organ is in trouble. The present invention utilizes this discovery to create an invention which is an improvement over the prior art of Chinese pulse feeling.

In one aspect of the invention, there is provided a method for monitoring the circulation of blood in a human body having a blood pressure pulse, and to optionally monitor the effectiveness of administering a medical treatment to the human body, comprising the steps of: (a) using a pressure transducer to sense the blood pressure pulse in an artery of the body, and produce an electrical pulse representing the blood pressure pulse; (b) using a spectrum analyzer to analyze the frequency spectrum of the electrical pulse in order to display amplitude, frequency, and phase of resonant components of the electrical pulse; (c) associating the spectral frequencies with selected organs and tissues of the as predetermined by prior correlation with medical diagnoses and the establishment of a normal spectral pattern; and (d) comparing the harmonic components in the analyzed spectrum to the harmonic components in a normal spectral pattern in order to determine whether or not an organ has abnormal blood circulation.

The method may include the further steps of: (e) after the comparing step, and upon determining that an organ has abnormal blood circulation, administering treatment to the human body intended to improve the condition of the organ having abnormal blood circulation; (f) repeating steps (a) through (d); and (g) evaluating the effectiveness of administering the treatment by comparing the results of each comparing step (d).

The method step (b) may include displaying standard deviation of the measured resonant components.

In another aspect of the invention, there is provided an apparatus for analyzing the blood pressure wave in an artery of the blood circulation of a body, the blood pressure wave having a frequency spectrum comprised of harmonic components, each component having a frequency and a relative phase angle, the apparatus comprising: pressure transducer means adapted to be operatively coupled to a surface of the body for measuring the blood pressure wave of blood flowing through the artery and outputting an electrical pulse representative of the blood pressure wave; and signal analyzer means coupled to and receiving the electrical pulse outputted from the pressure transducer means. The signal analyzer means comprises: means for receiving the outputted electrical pulse from the pressure transducer and analyzing the frequency spectrum of the electrical pulse representing the blood pressure wave in the artery to identify the frequency and relative phase angle of all harmonic components corresponding to respective harmonic frequencies of organs or tissues of the body; and means, coupled to the means for analyzing, for diagnosing an organ or tissue by determining whether or not the organ or tissue is physically abnormal from the amplitude and phase of the analyzed harmonic components, as compared with the amplitude and phase of analyzed harmonic components of a normal, healthy body, at a prescribed relative spectral frequency.

The transducer may be adapted to be operatively coupled to the surface of the artery at different locations on the body; and the signal analyzer may include means for diagnosing the condition of blood circulation at different branches of different arteries by analyzing phase and amplitude distribution from the different locations.

The signal analyzer may comprise harmonics analyzing means for analyzing the harmonics of the heartbeat by Fourier transform techniques.

The harmonic for the liver is known to be the first harmonic of the heartbeat, and the harmonics analyzing means evaluates the circulation condition of the liver and its related meridian.

The harmonic for the kidney is known to be the second harmonic of the heartbeat, and the harmonics analyzing means evaluates the circulation condition of the kidney and its related meridian.

The harmonic for the spleen is known to be the third harmonic of the heartbeat, and the harmonics analyzing means evaluates the circulation condition of the spleen and its related meridian.

The harmonic for the lung is known to be the fourth harmonic of the heartbeat, and the harmonics analyzing means evaluates the circulation condition of the lung and its related meridian.

In a further aspect of the invention there is provided a method for developing a new medical treatment of a human body, comprising the steps of: (a) employing a pressure transducer to sense, in a human body having a blood pressure pulse, the blood pressure pulse in an artery of the body, and produce an electrical pulse representing the blood pressure pulse; (b) using a spectrum analyzer to analyze the frequency spectrum of the electrical pulse in order to display amplitude, frequency, and phase of harmonic components of the electrical pulse; (c) associating the spectral frequencies with selected organs and tissues of the body as predetermined by prior correlation with medical diagnoses and the establishment of a normal spectral pattern; (d) comparing the harmonic components in the analyzed spectrum to the harmonic components in a normal spectral pattern in order to determine whether or not an organ has abnormal blood circulation; (e) after the comparing step, and upon determining that an organ has abnormal blood circulation, administering treatment to the human body intended to improve the condition of the organ having abnormal blood circulation; (f) repeating steps (a) through (d); (g) evaluating the effectiveness of administering the treatment by comparing the results of each the comparing step (d); (h) repeating steps (a) through (g) until the amount and rate of the effectiveness of the treatment have stabilized; (i) altering an aspect of the treatment; (j) repeating steps (a) through (h); and (k) evaluating the results of each step (h) to determine the best treatment for improving the condition of the organ having abnormal blood circulation.

The administering step (e) may comprise administering a drug into the human body; the altering step (i) may comprise altering the formula of the drug being administered; and the evaluating step (k) is performed to determine the formula for the drug that resulted in the best amount and rate of effectiveness of the drug treatment.

In yet another aspect of the invention there is provided a method for monitoring the circulation of blood in a human body having a blood pressure pulse, and to optionally monitor the effectiveness of administering a medical treatment to the human body, comprising the steps of: (a) monitoring the circulation of blood by employing a pressure transducer to sense the blood pressure pulse in an artery of the body, and produce an electrical pulse representing the blood pressure pulse; (b) using a spectrum analyzer to analyze the frequency spectrum of the electrical pulse in order to display amplitude, frequency, and phase of harmonic components of the electrical pulse; (c) associating the spectral frequencies with selected organs and tissues of the body as predetermined by prior correlation with medical diagnoses and the establishment of a normal spectral pattern; and (d) comparing the harmonic components in the analyzed spectrum to the harmonic components in a normal spectral pattern in order to determine whether or not an organ is receiving insufficient oxygen supply.

The method may include the further steps of: (e) after the comparing step, and upon determining that an organ has abnormal blood circulation, administering treatment to the human body intended to improve the condition of the organ having abnormal blood circulation; (f) repeating steps (a) through (d); and (g) evaluating the effectiveness of administering the treatment by comparing the results of each the comparing step (d).

The method step (b) includes displaying standard deviation of the measured harmonic components.

DETAILED DESCRIPTION OF THE PREFERRED EMBODIMENTS

Figure 1:
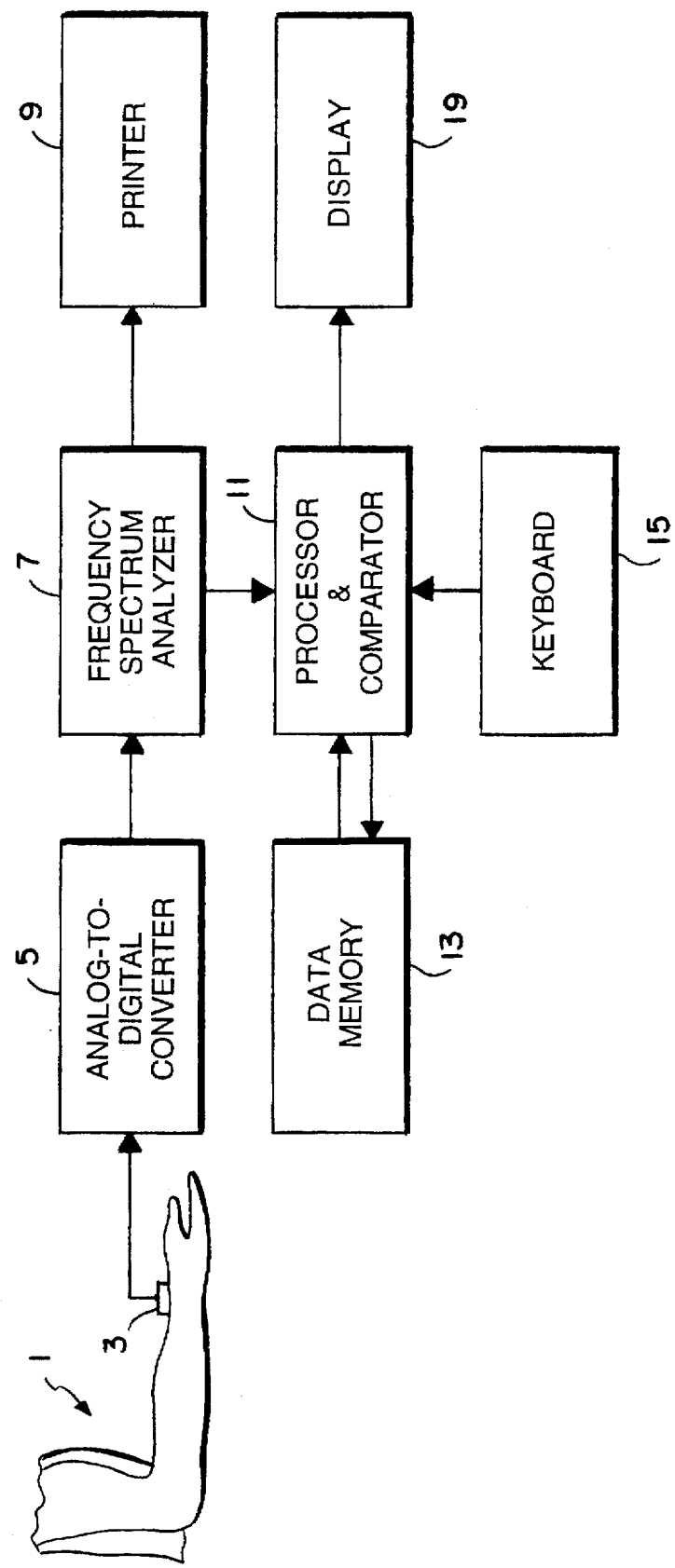
FIG. 1 shows a typical apparatus arrangement which will provide either a printed output from the spectrum analyzer or a display of the comparison between measured and normal harmonic resonant frequency components of the spectrum analyzed heartbeat pulse.

The disadvantage of Chinese pulse feeling over the current invention was that it failed to provide a systematic method to determine the flow of blood to the various organs. The success or failure of the method was completely determined by the skill of the pulse feeler. Such pulse feeler would invest many years in training; however, there was no way to insure that their results were accurate.

Because data can be analytically processed according to this invention, several groups of data can be generated, analyzed, and correlated to describe different conditions in the circulatory system:

(1) A weak amplitude in a specific spectral frequency component indicates softness of an organ or tissue in the meridian, or the leak of energy that is intended to be transmitted toward that meridian. This may happen when the arteries in the tissue, or adjacent the tissue, are blocked or restricted and the blood flow toward the organ or tissue is reduced.

(2) An increase of the amplitude in a specific spectral frequency component indicates stiffness of the organ or tissue in the meridian, or the increase of the energy that is transmitted toward that meridian. This may happen when infection or other physiological disturbance of the body demands more blood, so that the blood moving toward the organ or tissue will be increased.

(3) A change of the phase in a specific spectral frequency component indicates that the stiffness or the compliance of the organ or tissue in the meridian is changed which implies that the structure of the organ or tissue changed or that the coupling between arteries is change.

(4) A change of the standard deviation in a specific spectral frequency component indicates how much the sphincter at the terminal of the artery is opened. The larger the standard deviation the more the terminal sphincter will open which implies the organ or tissue lacks oxygen in the corresponding meridian.

Actually, Chinese medicine was largely developed according to these principles that are based on the meridian and circulatory theory. The symptoms of ailing patients, for example, were described according excess energy of the liver meridian, excess energy of the stomach meridian, lack of energy of the kidney meridian, etc. Moveover, different physiological problems may be diagnosed from this disorder in circulation.

All such descriptions or diagnoses can be found in Chinese medical books, such as *Yellow Emperor's Internal Medicine* (黃帝內經)

The relationship between the diagnosis in a meridian sense and diagnosis in an organ is highly correlated but is not 100%. One reason is the nonlinear interactions between organs of the human body versus a linearized diagnostic system (the meridian system is a linear solution). Other reasons can be: (1) The meridian includes organs and a group of acupuncture points, and sometimes damage of the acupuncture point or several acupuncture points can show up in the pulse diagnosis while the organ is still healthy, but in the long run, the organ will be deteriorated due to unbalanced blood circulation; or (2) A problem in one organ may slowly affect the health of the other organs. Experience is needed in order to judge the cause and consequences of these multiple problems, and most of the rules are described in Chinese medicine books.

Another most effective use of this diagnosis method can be monitoring the effect of a treatment, whether or not the problem in the meridian is from the organ or acupuncture points, or is a multiple meridian problem. An effective treatment will bring the pulse spectrum back to normal.

Therefore this monitoring procedure can be used to develop new treatments such as drugs, excise, or energy transmission devices such as acupuncture or a synchronized energy source.

FIG. 1 shows a typical apparatus arrangement in which a subject 1 is being monitored for analysis of the subject's heartbeat pulse in order to assess the health of the various organs and/or tissue of the subject.

A transducer 3 is coupled to an artery of the subject 1, and in the example of FIG. 1, the transducer 3 is pressed against the inside of the wrist of the subject so as to sense the pulse of the heartbeat in a convenient and noninvasive manner.

The output of transducer 3, being an analog electrical signal, is sent to an analog-to-digital converter 5 for converting the analog signal into more conveniently processed digital information. The heartbeat pulse digitized signal from converter 5 is applied to the input of a frequency spectrum analyzer 7 which is a piece of equipment well known to one of ordinary skill in the art. Analyzer 7 typically has its own display screen for viewing the resonant frequency components of the analyzed input signal, and in this case, the harmonic frequency components of the heartbeat pulse. In a typical setup, a printer 9 may be driven by the spectrum analyzer 7 in order to have a hard copy printout of the analyzed results which were viewed on the display screen of the spectrum analyzer 7.

In accordance with the invention, the output of the spectrum analyzer 7 is also sent to a processor and comparator 11 which either includes as part of its configuration, or as a separate unit, a data memory 13. Memory 13 holds information stored in it by an operator inputting information from a keyboard 15 through processor and comparator 11. The operator (not shown) will have previously inputted through keyboard 15 diagnostic information relating to the testing of a large number of subjects who have known normal internal organs and tissues. The data memory 13 will then store this information for retrieval later when comparing the normal frequency component characteristics with the frequency component characteristics of the subject 1 being analyzed or treated.

As with any processor/memory arrangement, a display 19 can be provided to display the results of the information being stored in data memory 13 or the results of the processing of input signals to processor and comparator 11.

Basically, when a subject 1 is to be examined and diagnosed, the appropriate "normal" information (i.e. data from an established normal healthy subject) is retrieved from data memory 13 and held in processor and comparator 11 for ultimate comparison purposes. The reading of the spectrum analyzer 7, coupled to the subject 1 under test, is sent to processor and comparator 11 for comparison with the retrieved "normal" data from memory 13. When the comparison is completed, the results are displayed on a display 19. The information that is viewable on display 19 is then analyzed by the practitioner to determine which frequency components show abnormal characteristics, and it is this information which permits the practitioner to determine a failing organ or tissue in the subject 1 and make appropriate determinations for treatment of the subject 1. Over time, treatment of the subject and repeated analysis will give insight to the effectiveness of the treatment.

The harmonics of the heartbeat pulse may be analyzed, for example, by signal analyzer 7 using Fourier transform techniques. From research, it has been determined that the Fourier transformed spectrum from the heartbeat pulse of a normal person is as follows: (The normalized amplitude is 100%*Cn/C0. The unit of phase angle is shown in degrees).

| n | Amp (Cn) | Nor. Amp | Phase Angle |
|---|---|---|---|
| 0 | 1766.34277 | 100.00000 | 0.00000 |
| 1 | 1505.68213 | 85.24292 | 102.34065 |
| 2 | 876.61273 | 49.62896 | 137.17479 |
| 3 | 399.75214 | 22.63136 | 179.60005 |
| 4 | 269.97833 | 16.81318 | −172.97724 |
| 5 | 191.11801 | 10.81998 | −124.90088 |

-continued

| n | Amp (Cn) | Nor. Amp | Phase Angle |
|---|---|---|---|
| 6 | 81.61549 | 4.62059 | −98.57288 |
| 7 | 48.29361 | 2.73410 | −88.55642 |
| 8 | 29.18774 | 1.65244 | −67.01342 |
| 9 | 14.31484 | 0.81042 | −41.34580 |
| 10 | 4.60961 | 0.26097 | −18.09173 |
| 11 | 5.21830 | 0.31241 | −27.30604 | where:

n=frequency number (C0–C11, C0 being the fundamental frequency of the heartbeat, C1 being the first harmonic, C2 being the second harmonic, etc.)

Amp=amplitude

Nor. Amp=normalized amplitude

Phase Angle=angular phase difference between the fundamental heartbeat pulse and the harmonic component

EXAMPLES (1) This invention can be used to diagnose the circulation condition of the human body.

To diagnose a patient, the patient does not take any medicine within two days of examination. This is an important precaution, because the medicine that cures an illness usually will cause the pulse characteristics to shift in a specific direction and create ambiguity in any decision based on test results.

Example (1-A):

The fifth harmonic is related to the stomach meridian; a patient with an upset stomach will have abnormal fifth harmonic. There are two kinds of stomach problem: (1) excess acid, and (2) insufficient blood circulation. These problems usually need gastric fluid analysis to see if the pH is abnormal. However, by using pulse diagnosis, these two problems can be easily differentiated. If the amplitude is too large, the stomach has excess acid. If the amplitude is too small, the blood circulation of the stomach is weak.

Example (1-B):

The first harmonic is related to the liver meridian; however, the liver meridian may be related to many different circulatory problems. Many of the problems of the body are induced by a liver problem, and some of the problems in other organs may cause a liver problem. According to Chinese medicine, the weakness of lung meridian (the fourth harmonic) will cause a hyper-liver meridian. When the liver is really in trouble, it will affect the spleen meridian (the third harmonic) and cause weakness of this meridian. This is understandable.

A weak lung will cause an insufficient oxygen supply; therefore some metabolisms are not completely cleaned by the body, and the enzymes in the liver are required to convert them to final products so the blood flowing toward the liver will be increased, causing a hyper-liver meridian. When the fourth harmonic, C4, becomes −, the first harmonic, C1, will usually become + due to physiological balance. This + sign for C1 is not due to a liver problem but to a lung problem. Therefore, to test for the liver problem the criterion C1+C4≧X+ is used, together with the criterion C1≧3+, and X was found out by experiments to be 4. That a liver problem will affect other organs, especially in the digestive system, is also commonly described in medicine textbooks (A. C. Guyton, M.D., *Human Physiology and Mechanism of Disease*, W. B. Saunders Company, 1992). When considering only the liver and the lung, and use the following criteria in the diagnosis (Note: The criterion used in the following tables are determined by experiments. In clinical tests, when one parameter is known to relate to one kind of disease, typical values can be established. For example, SGOT or SGPT is related to liver problems, and the values of 40μ/dl or 35μ/dl was determined by experiments. For different members of the human race, these values may change slightly.):

| Total Bilirubin | (T. Bil) > 1.3 mg/dl |
|---|---|
| Direct Bilirubin | (D. Bil) > 0.5 mg/dl |
| Serum glutamic oxaloacetic transaminase | (SGOT) > 40 μ/dl |
| Serum glutamic pyruvic transaminase | (SGPT) > 35 μ/dl | as abnormal for a blood test, and (1) C1≦3−, (2) C1≧3+, and (3) C1+C4≧4+ (for C1, for every 5% above standard, one + is given, and for every 5% below standard, one − is given; for C4, for every 10% above standard one + is given, and for every 10% below standard, one − is given), it was found that in 70 subjects:

|  | Blood test abnormal | Blood test normal | Total |
|---|---|---|---|
| Pulse abnormal | 10 | 4 | 14 |
| Pulse normal | 5 | 51 | 56 |
| Total | 15 | 55 | 70 |

If the statistical significance is checked by $\chi^2$– test,

|  | Blood test abnormal | Blood test normal | Total |
|---|---|---|---|
| Pulse abnormal | 10 (3) | 4 (11) | 14 |
| Pulse normal | 5 (12) | 51 (44) | 56 |
| Total | 15 | 55 | 70 |

In the parentheses () are the expected values of one test, that is, from the pulse test, 14/70=occurrence of abnormal pulse detection. For 15 blood tests, the abnormal rate will be 3, and normal rate will be 12. The value 3 was calculated by the formula 15×(14/70)=3 (This kind of $\chi^2$– data can be found in most statistical books.) For 55 blood tests, the abnormal rate will be 11, and the normal rate will be 44.

$$\chi^2 = \Sigma[(O-E)^2/E]$$

O=observation value, E=expected value

Substituting the values in the above table into the $\chi^2$ equation, the result is $\chi^2$=25.97. From the $\chi^2$ table in a statistics book, which shows P (probability) <0.001, the pulse diagnosis is shown to significantly correlate with the blood tests. (When P<0.05, this implies statistical significance, and the smaller the P, the higher the correlation.)

However, there is still some difference between the blood tests and the pulse diagnoses.

If the spleen meridian is also taken into consideration and one more criterion for abnormal is added, that is C3≦3− and C1≧3+ (for C3, for every 10% below normal one − is given), resulting in 3 more pulse abnormal persons. The table becomes

|  | Blood test abnormal | Blood test normal | Total |
| --- | --- | --- | --- |
| Pulse abnormal | 13 | 4 | 17 |
| Pulse normal | 2 | 51 | 53 |
| Total | 15 | 55 | 70 |

And the correlation becomes even better.

Further, If the gallbladder meridian is considered, there will be 4 more abnormal persons, and one can therefore detect all the blood test abnormal patients, but the number in the category of pulse abnormal and blood test normal also becomes larger. This is also reasonable.

To test the liver problem, the T-Bil, D-Bil, SGOT, and SGPT are just a few of the most sensitive blood tests. There are other blood tests such as alkaline phosphatase (Alp), zinc sulfate turbidity test (ZTT), α-feto-proptein (AFP), leucine amino peptidase (LAP), hepatitis B surface Antigen (HBsAg), etc. Even ultra-sound or radiology tests can also give indication of a liver problem.

Different liver problems may be sensitive to different tests, and these problems may change the blood circulation to different extents. The same is also true for the pulse diagnosis criterion; a different criterion implies a different problem.

This is the essence of Chinese medicine, the diagnosis actually gives direct suggestions for treatment, not all liver problems are from the same source and should not be treated the same way.

So the major effort of a treatment for liver problems in Chinese medicine is to treat the liver directly, and this has an effect primarily on the frequency C1, but minor aspects of the treatment will be directed toward lung, spleen, or gall-bladder meridian to cure the induced problems in these organs, so that the blood circulation can be normalized in the body as a whole.

Example (1-C):

A migraine headache without detectable physiology problems can be detected by the observation of an abnormal standard deviation at the 6th harmonic. If the left side shows a large standard deviation, this implies the disorder is at the patient's left side, and the same is true at the right side. If both sides show large standard deviation, the subject will feel dizzy when he or she is tired or in a close area.

A mean standard deviation of $\geq 15\%$ for 5 consecutive pulses is considered as the criteria for the lack of blood supply to the head. The accuracy is 90%. To check which side has a headache, the accuracy is 100%.

Here again, the energy distributed to the lung meridian has an effect on this diagnosis. If the lung meridian is normal, the 15% figure is a good decision scale; if the lung meridian-is abnormal, the subject feels a headache at a lower value than 15%.

From mathematics, the fourier components are orthonormal to each other. Each meridian is related to one Fourier component which implies that each meridian is independent of other meridians. However, the circulatory system is an almost linear system, the non-linear weight being about 10%. Therefore, interrelation between meridians can be expected by the non-linear interactions such as second harmonic generation, or sum-frequency in physics. Because analyzing the pulse is tantamount to diagnosing the circulation condition, while other markers such as SGOT, SGPT assess the damage of the liver cells, etc., the correspondence may not be unique and linear. The diagnosis implied from this apparatus are the same as the diagnosis in Chinese medicine. The Chinese medicine diagnosis principles are rather fuzzy. The pulse feeling interpretation is not always clear so as to obscure making proper medical decisions, and the meridians are related to each other through the mother-and-son law (a non-linear interaction) or anatomic interrelation, such as liver and gall-bladder, kidney and bladder. These two organs are close to each other, and some arteries that supply blood to them are common, or some tissues are closely attached to each other. However, the general rule for diagnosis is that the larger the deviation from the normal value, the more serious is the problem. One may find all the rules in text books relating to Chinese medicine.

The mother and son law is a non-linear interaction of waves A+B→C, i.e. wave of frequency A mixed with wave of frequency B to produce wave of frequency C.

From conservation of energy, $$E_A + E_B = E_C. \quad E=\text{energy}$$

From conservation of momentum, $$A+B=C.$$

In the non-linear interaction, second harmonic generation is always with large cross section $$1+1 \rightarrow 2 \quad 2+2 \rightarrow 4 \quad 3+3 \rightarrow 6 \ldots$$

are the more important transitions.

From conservation of energy, $$2E_1 = E_2.$$

Therefore, when $E_1 \uparrow \rightarrow E_2 \downarrow$, this makes the wave with frequency 1 and wave with frequency 2 share energy with and help each other. While the 1+3→4 or 2+3→5, in the sum frequency rule, if the $E_4$ is conserved, then $E_1 \uparrow \rightarrow E_3 \downarrow$. This implies frequencies 1 and 3 will interfere with each other, as do frequencies 2 and 3.

From the resonant frequencies, it was found for all the meridians that these are consistent with the mother and son law rule in Chinese medicine which assigns wood to liver, water to kidney, earth to spleen . . . , the wood helps water, while water interferes with earth. (For details, see "The relation between meridian and energy distribution" by W. K. Wang, Y. Y. Lin Wang, T. L. Hsu, and Y. Chiang, Proceeding of the first international conference on bioenergetic medicine past, present and future, Honolulu, Hi., USA, pp. 302–316, 1991).

(2) The apparatus of this invention can be used as a monitor of the effectiveness of treatment.

Example (2-A):

Patients with kidney problems are found to have abnormal second and third harmonics, and the renal failure patients all have 5 − or more − in the pulse diagnosis (every 10% below normal is given one −). This 5 − is the sum value of the second harmonic and third harmonic. The reverse is not true; not all persons with 5 − in the second and third harmonic have renal failure. Because the second harmonic is also related to the blood flow toward the legs, circulatory problems in the legs or feet all show an abnormal second harmonic, while the third harmonic is also related to the digestive ability and other parts of the body. Accordingly, the renal circulation is not exclusively indicated by an analysis of the second and third harmonics but is an important part thereof. For minor renal problems, some patients showed − only at the second harmonic and some showed − at the third harmonic. The treatment should therefore be different as between patients. This is also taught in Chinese medicine. No matter what treatment is being used, this apparatus may be used to monitor the treatment. If the number of − signs is reduced gradually, this implies the patient is getting better and recovering, and vice versa.

For other circulatory problems, once the problems are diagnosed by this apparatus (or the problems are diagnosed by other methods or instruments and confirmed by this apparatus), the effectiveness of administering treatment may be monitored evaluated by analyzing the blood flow pulse. If the treatment returns the pulse of the patient toward normal, this implies that it is a good treatment.

(3) The apparatus can be used as a tool to develop new treatments.

This is an extension of the usage in Example 2(A) above. Besides human subjects, one may also use animal models to study the effect of a treatment, and therefore develop a new treatment by intelligent analysis of results, trial-and-error procedures, time-progress charting, and similar procedures can be used as a tool to develop new drugs. A drug may simply be considered as one of the treatments; however, administering drugs is the most popular of medical treatments. The apparatus and method of the present invention can be systematically used to perform screening tests to track the effectiveness of different drugs and to lead to the discovery of new drugs.

I claim:

1. A method for monitoring the circulation of blood in a human body having a blood pressure pulse, comprising the steps of:

(a) using a pressure transducer to sense the blood pressure pulse in an artery of the body, and produce an electrical pulse representing the blood pressure pulse;

(b) using a spectrum analyzer to analyze the frequency spectrum of said electrical pulse in order to display amplitude, frequency, and phase of harmonic components of said electrical pulse;

(c) associating the spectral frequencies with selected organs and tissues of the body as predetermined by prior correlation with medical diagnoses and the establishment of a normal spectral pattern; and (d) comparing the harmonic components in the analyzed spectrum to the harmonic components in a normal spectral pattern in order to determine whether or not an organ has abnormal blood circulation.

2. The method as claimed in claim 1, wherein said step (b) includes displaying standard deviation of the measured harmonic components.

3. A method for monitoring the circulation of blood in a human body having a blood pressure pulse, and to evaluate the effectiveness of administering a medical treatment to the human body, comprising the steps of;

(a) using a pressure transducer to sense the blood pressure pulse in an artery of the body, and produce an electrical pulse representing the blood pressure pulse;

(b) using a spectrum analyzer to analyze the frequency spectrum of said electrical pulse in order to display amplitude, frequency, and phase of harmonic components of said electrical pulse;

(c) associating the spectral frequencies with selected organs and tissues of the body as predetermined by prior correlation with medical diagnoses and the establishment of a normal spectral pattern;

(d) comparing the harmonic components in the analyzed spectrum to the harmonic components in a normal spectral pattern in order to determine whether or not an organ has abnormal blood circulation:

(e) after said comparing step, and upon determining that an organ has abnormal blood circulation, administering treatment to the human body intended to improve the condition of the organ having abnormal blood circulation;

(f) repeating steps (a) through (d); and (g) evaluating the effectiveness of administering the treatment by comparing the results of each said comparing step (d).

4. An apparatus for analyzing the blood pressure wave in an artery of the blood circulation of a body, the blood pressure wave having a frequency spectrum comprised of harmonic components, each component having a frequency and a relative phase angle, said apparatus comprising:

pressure transducer means adapted to be operatively coupled to a surface of the body for measuring the blood pressure wave of blood flowing through the artery and outputting an electrical pulse representative of the blood pressure wave; and signal analyzer means coupled to and receiving the electrical pulse outputted from said pressure transducer means, said signal analyzer means comprising:

means for receiving said outputted electrical pulse from said pressure transducer and analyzing the frequency spectrum of the electrical pulse representing the blood pressure wave in the artery to identify the frequency and relative phase angle of all harmonic components corresponding to respective harmonic frequencies of organs or tissues of the body; and means, coupled to said means for analyzing, for diagnosing an organ or tissue by determining whether or not the organ or tissue is physically abnormal from the amplitude and phase of said analyzed harmonic components, as compared with the amplitude and phase of analyzed harmonic components of a normal, healthy body, at a prescribed relative spectral frequency.

5. An apparatus as set forth in claim 4, wherein:

said transducer is adapted to be operatively coupled to the surface of the artery at different locations on the body; and said signal analyzer includes means for diagnosing the condition of blood circulation at different branches of different arteries by analyzing phase and amplitude distribution from said different locations.

6. An apparatus as set forth in claim 4, wherein said signal analyzer comprises harmonics analyzing means for analyzing the harmonics of the heartbeat by Fourier transform techniques.

7. An apparatus as set forth in claim 6, wherein said harmonic for the liver is the first harmonic of the heartbeat, and said harmonics analyzing means evaluates the circulation condition of the liver and its related meridian.

8. An apparatus as set forth in claim 6, where said harmonics analyzing means evaluates the circulation condition of the kidney and its related meridian by analyzing said second harmonic of said heartbeat.

9. An apparatus as set forth in claim 6, wherein said harmonic for the spleen is the third harmonic of said heartbeat, and said harmonics analyzing means evaluates the circulation condition of the spleen and its related meridian.

10. An apparatus as set forth in claim 5, wherein said harmonic for the lung is the fourth harmonic of said heartbeat, and said harmonics analyzing means evaluates the circulation condition of the lung and its related meridian.

11. A method for developing a new medical treatment of a human body, comprising the steps of:

(a) employing a pressure transducer to sense, in a human body having a blood pressure pulse, the blood pressure pulse in an artery of the body, and produce an electrical pulse representing the blood pressure pulse;

(b) using a spectrum analyzer to analyze the frequency spectrum of said electrical pulse in order to display amplitude, frequency, and phase of harmonic components of said electrical pulse;

(c) associating the spectral frequencies with selected organs and tissues of the body as predetermined by prior correlation with medical diagnoses and the establishment of a normal spectral pattern;

(d) comparing the harmonic components in the analyzed spectrum to the harmonic components in a normal spectral pattern in order to determine whether or not an organ has abnormal blood circulation;

(e) after said comparing step, and upon determining that an organ has abnormal blood circulation, administering treatment to the human body intended to improve the condition of the organ having abnormal blood circulation;

(f) repeating steps (a) through (d);

(g) evaluating the effectiveness of administering the treatment by comparing the results of each said comparing step (d);

(h) repeating steps (a) through (g) until the amount and rate of the effectiveness of the treatment have stabilized;

(i) altering an aspect of the treatment;

(j) repeating steps (a) through (h); and (k) evaluating the results of each step (h) to determine the best treatment for improving the condition of the organ having abnormal blood circulation.

12. The method as claimed in claim 11, wherein:

said administering step (e) comprises administering a drug into the human body;

said altering step (i) comprises altering the formula of the drug being administered; and said evaluating step (k) is performed to determine the formula for the drug that resulted in the best amount and rate of effectiveness of the drug treatment.

13. A method for monitoring the circulation of blood in a human body having a blood pressure pulse, comprising the steps of:

(a) monitoring the circulation of blood by employing a pressure transducer to sense the blood pressure pulse in an artery of the body, and produce an electrical pulse representing the blood pressure pulse;

(b) using a spectrum analyzer to analyze the frequency spectrum of said electrical pulse in order to display amplitude, frequency, and phase of harmonic components of said electrical pulse;

(c) associating the spectral frequencies with selected organs and tissues of the body as predetermined by prior correlation with medical diagnoses and the establishment of a normal spectral pattern; and (d) comparing the harmonic components in the analyzed spectrum to the harmonic components in a normal spectral pattern in order to determine whether or not an organ is receiving insufficient oxygen supply.

14. The method as claimed in claim 13, wherein said step (b) includes displaying standard deviation of the measured harmonic components.

15. A method for monitoring the circulation of blood in a human body having a blood pressure pulse, and to evaluate the effectiveness of administering a medical treatment to the human body, comprising the steps of:

(a) monitoring the circulation of blood by employing a pressure transducer to sense the blood pressure pulse in an artery of the body, and produce an electrical pulse representing the blood pressure pulse;

(b) using a spectrum analyzer to analyze the frequency spectrum of said electrical pulse in order to display amplitude, frequency, and phase of harmonic components of said electrical pulse;

(c) associating the spectral frequencies with selected organs and tissues of the body as predetermined by prior correlation with medical diagnoses and the establishment of a normal spectral pattern;

(d) comparing the harmonic components in the analyzed spectrum to the harmonic components in a normal spectral pattern in order to determine whether or not an organ is receiving insufficient oxygen supply:

(e) after said comparing step, and upon determining that an organ has abnormal blood circulation, administering treatment to the human body intended to improve the condition of the organ having abnormal blood circulation;

(f) repeating steps (a) through (d); and (g) evaluating the effectiveness of administering the treatment by comparing the results of each said comparing step (d).

* * * * *